US011510883B2

(12) United States Patent
Kirby (10) Patent No.: US 11,510,883 B2
(45) Date of Patent: Nov. 29, 2022

(54) KIT FOR DELIVERY OF AN ACTIVE COMPOUND INTO THE SKIN (71) Applicant: Xobaderm Limited, Cardiff (GB)

(72) Inventor: Andrew Kirby, Cardiff South Glamorgan (GB)

(73) Assignee: XOBADERM LIMITED, Cardiff (GB)

( * ) Notice: Subject to any disclaimer, the term of this patent is extended or adjusted under 35 U.S.C. 154(b) by 66 days.

(21) Appl. No.: 16/754,051

(22) PCT Filed: Oct. 8, 2018

(86) PCT No.: PCT/GB2018/052867
§ 371 (c)(1),
(2) Date: Apr. 6, 2020

(87) PCT Pub. No.: WO2019/069102
PCT Pub. Date: Apr. 11, 2019

(65) Prior Publication Data
US 2020/0323789 A1    Oct. 15, 2020

(30) Foreign Application Priority Data
Oct. 6, 2017    (GB) ...................................... 1716391

(51) Int. Cl.
*A61K 9/70*    (2006.01)
*A61K 9/00*    (2006.01)
(Continued)

(52) U.S. Cl.
CPC .......... *A61K 9/7084* (2013.01); *A61K 9/0014* (2013.01); *A61K 31/455* (2013.01);
(Continued)

(58) Field of Classification Search
None
See application file for complete search history.

(56) References Cited

U.S. PATENT DOCUMENTS

| 2012/0220980 A1* | 8/2012 | Ross ................. A61M 5/14248 604/506 |
| 2014/0220101 A1 | 8/2014 | Sanyal |
| 2016/0250241 A1* | 9/2016 | Deren-Lewis ....... A61K 31/706 514/43 |

FOREIGN PATENT DOCUMENTS

| EP | 1992386 A1 | 11/2008 |
| GB | 2533839 A | 7/2016 |

(Continued)

OTHER PUBLICATIONS

Mesotherapost Cellular Stimulation Program; Aug. 6, 2012; Mintel; XP055526101, retrieved from www.gnpd.com.

(Continued)

*Primary Examiner* — Dominic Lazaro
(74) *Attorney, Agent, or Firm* — Dinsmore & Shohl LLP (57) ABSTRACT

A kit for enabling delivery of an active compound to the skin for penetration into the skin, a delivery device for delivering an active compound, and a method of delivery of an active compound are provided. An active compound delivery kit for enabling delivery of an active compound into the skin of a subject includes an arrangement for providing a pathway into a biological barrier of a subject in an application zone, an active compound provided in dry form, and a delivery device for delivery of dissolved active compound to the application zone. Provision of a pathway into the biological barrier, preferably skin, is provided and the active compound applied in optimum form within a short time frame after forming the pathway ensuring treatment of the desired skin cells is optimised.

13 Claims, 3 Drawing Sheets

(51) Int. Cl.
  *A61K 31/7084*    (2006.01)
  *A61K 31/455*     (2006.01)
  *A61M 37/00*      (2006.01)

(52) U.S. Cl.
  CPC ..... *A61K 31/7084* (2013.01); *A61M 37/0015* (2013.01); *A61M 2037/0023* (2013.01); *A61M 2202/064* (2013.01)

(56) References Cited

FOREIGN PATENT DOCUMENTS

| WO | 2004039428 A2 | 5/2004 | | |
|----|---------------|--------|---|---|
| WO | 2005042054 A2 | 5/2005 | | |
| WO | 2008091602 A2 | 7/2008 | | |
| WO | 2011016615 A2 | 2/2011 | | |
| WO | WO-2011016615 A2 * | 2/2011 | ........ | A61M 37/0015 |
| WO | 2012131623 A2 | 10/2012 | | |
| WO | 2013014549 A1 | 1/2013 | | |
| WO | 2018003952 A1 | 1/2018 | | |

OTHER PUBLICATIONS

Review of Patents for Microneedle Application Devices Allowing Fluid Injections Through the Skin; Lhernould Marion, Tailler Serge, Deleers Michel, Selchambre Alain; Recent Pat Drug Deliv Formul., vol. 9, No. 2, Jun. 1, 2015, pp. 146-157, XP002786834.
International Search Report dated Feb. 13, 2019, International Application No. PCT/GB2018/052867.
United Kingdom Search Report; Application No. GB1716391.6.

* cited by examiner

KIT FOR DELIVERY OF AN ACTIVE COMPOUND INTO THE SKIN

CROSS-REFERENCE TO RELATED APPLICATIONS

This application is the U.S. national stage of PCT/GB2018/052867 filed Oct. 8, 2018, which claims priority of United Kingdom Patent Application 1716391.6 filed Oct. 6, 2017 both of which are hereby incorporated by reference in their entirety.

FIELD OF THE INVENTION

The present invention relates to a kit for enabling delivery of an active compound to the skin for penetration into the skin, and a method of delivery of an active compound.

BACKGROUND OF THE INVENTION

There are many known formulations provided as creams, gels, serums, lotions, ointments for providing a large variety of effects to the skin. These include for example active compounds such as peptides dissolved in a carrier for enhancing collagen synthesis with the aim of reducing the appearance of aging, and ascorbic acid (stabilised vitamin C).

The stratum corneum is the outermost layer of the epidermis, consisting of dead skin cells called corneocytes. This layer is composed of 15-20 layers of flattened cells with no nuclei and cell organelles. These corneocytes are embedded in a lipid matrix composed of ceramides, cholesterol, and fatty acids, and provide the tough outer surface of the skin. This is moderately abrasion resistant and prevents foreign matter ingress to the underlying skin layers. This provides difficulty in transferring active components to the cells beneath the stratum corneum.

A solution to this is to add chemical compounds to the formulations such as penetration enhancers which effectively bury themselves into the lipid layers creating a pathway for the desired active component to travel. They exert their effect by using a range of mechanisms including disrupting the lipid bilayer structure in the stratum corneum by insertion into these structures and disrupting packing (e.g Azone® and oleic acid), or by extracting lipids from the stratum corneum (e.g. DMSO or ethanol) thereby forming aqueous channels, or by altering the solvent nature of the stratum corneum and consequently modifying the drug partitioning coefficient, or acting on intracellular keratin in corneocytes (e.g. ionic surfactants and DMSO), or other mechanisms. However, many chemical penetration enhancers have a limited use in topical and transdermal delivery systems because they can cause skin irritation.

A further option is to apply a microneedle array to the skin prior to application of the formulation to provide pathways through the stratum corneum. This improves the ability for the active compound to penetrate through the outer layers and reach the target of the active compound, by creating temporary micro-channels.

A further problem however with some active compounds is the tendency to degrade in water. Accordingly, further additives such as preservatives and anti-oxidants are incorporated into a topical dosage form in an effort to maintain the active compound preserved in solution such that when applied to the skin the desirable benefits are achieved. This is undesirable as consumers often seek a purer and simpler formulation, with as few additives as possible, and also for some active compounds this is ineffective as the tendency to degrade cannot be overcome by additives. This may lead to an unacceptably short shelf life. A solution is therefore sought that can allow delivery of actives, particularly those with high water solubility and low stability, without excessive use of chemical penetration enhancers, preservatives, anti-oxidants and other additives.

SUMMARY OF THE INVENTION

According to an aspect of the present invention there is an active compound delivery kit for enabling delivery of an active compound into the skin of a subject, the kit comprising:
  an arrangement for providing a pathway into a biological barrier of a subject in an application zone;
  an active compound provided in dry form;
  a delivery device for delivery of dissolved active compound to the application zone.

The claimed invention means that a user has the active compound in a stable dry form, and can be hydrated and/or dissolved for immediate use meaning the active compound does not have time to disassociate or degrade. The ability to provide a pathway into the biological barrier, preferably skin, and apply the active compound in optimum form within a short time frame after forming the pathway ensures treatment of the desired skin cells is optimised.

The biological barrier is beneficially the skin, and may comprise one or more of the stratum corneum, mucous membrane and others. It is preferable however that at least penetration into, and potentially through and beyond the stratum corneum is achieved.

The active compound is beneficially soluble, and even more beneficially water soluble. The active compound preferably comprises a precursor to nicotinamide adenine dinucleotide (NAD+). NAD+ is used by cells in ATP synthesis where it is cycled between NAD+ and NADH, but it is also used as a substrate and therefore consumed by repair and maintenance enzymes PARP and Sirtuins. NAD+ levels form part of a network of pathways that are involved in DNA repair, energy generation, inflammation, chromosomal stability and longevity. As we age, the cellular levels of NAD+ decline and so these pathways can fail to function. Human skin is exposed to daily environmental insults, particularly solar radiation, that triggers a range of molecular responses that can lead to cellular dysfunction and, ultimately skin aging (photoaging). One of the responses is increased oxidative stress that damages multiple cellular structures and can deplete NAD+ and ATP. Cellular NAD+ pools are lower in aged skin and treatment with an active compound such as Nicotinamide Riboside NR or other NAD+ increasing metabolites such as nicotinamide, nicotinic acid, nicotinamide mononucleotide and others may restore these levels, thereby mitigating cellular bioenergetic dysfunction. This ultimately improves the cosmetic appearance of aging of the skin and protects the skin from further damage and deterioration. It will therefore be appreciated that it is beneficial that the active compound stimulates NAD+ levels.

The active compound preferably comprises nicotinamide and/or a derivative of nicotinamide. Even more beneficially the active compound comprises one or more of nicotinamide riboside (NR) and nicotinamide mononucleotide (NMN). NR and NMN are known and NR currently ingested orally by humans as a supplement for increasing health and well-being through multiple organ systems, and it has been determined that such an active compound may be used for localised application to the skin. In cells, NR or NMN combine with phosphate and subsequently with adenosine to form (NAD+). Neither NR nor NMN have previously been utilised for topical application to the skin as there has been no means of enabling delivery. The provision of NR or NMN in dried form means it can be transported and stored without disassociation or degradation, and can be activated when required. Furthermore the ability to provide a pathway into the skin with the kit according to the present invention means that delivery can be successfully achieved where otherwise the skin would provide a barrier to penetration.

The active compound may comprise or further comprise one or more of ascorbic acid (vitamin C), peptides, growth factors, anti-glycation actives, skin lightening agents, vitamins, retinoids, flavonoids, anti-oxidants, sirtuin activating compounds, polyphenols, and/or polyamines.

The active compound is preferably provided in dry powdered form. The active compound may be in a dried form adhered to the delivery device.

The delivery device may comprise a liquid absorbent carrier of the dry active compound. The carrier may be termed a substrate for carrying the dry active compound. The carrier can be drawn across or dabbed or held onto the skin. The delivery device may comprise a patch or pad.

The delivery device preferably comprises a structure having a plurality of interstices therein for receipt of the dry active compound. The delivery device may take a variety of forms such as sponges and foams for example. The delivery device may comprise a first portion and a second portion and where the active compound is provided between the first and second portion. The first and second portion may be stacked. The first and second portion preferably define a pocket therebetween for receipt of the active compound. The pocket may be formed by adhering the first and second portion adjacent a peripheral edge in a stacked configuration.

The kit preferably further comprises a liquid dispensing arrangement for dispensing a liquid to the active compound in dry form for hydrating and/or dissolving the active compound to provide dissolved active compound. This assists a user in ensuring the active compound is dissolved or hydrated with a known clean and sterile liquid, the liquid typically water based. The term liquid includes semi liquids such as gels, lotions, emulsions or creams. The liquid is preferably a solvent.

Accordingly the active compound is dissolved into the liquid. The liquid may be a hyaluronic acid solution. The liquid preferably has low bioburden. The liquid is preferably sterile. The liquid dispenser is preferably arranged to stop microorganisms getting into/out of the liquid in order that no preservatives are needed in the liquid.

The kit preferably further comprises a cleaning arrangement for cleaning the arrangement for providing a pathway into the biological barrier. The cleaning arrangement may take various forms such as one or more individually wrapped cleaning patches carrying a sterilising agent, a bath of cleaning fluid which may be alcohol for example, or an absorbent pad carrying sterilising fluid. The provision of a cleaning arrangement in the kit means that after application to the skin the arrangement for providing a pathway into the biological barrier may be cleaned and stored for repeated future use. A repeated usage of for example microneedles is useful in reducing waste and cost associated with single use devices.

The kit preferably further comprises a sealed housing for housing the arrangement for providing a pathway into the biological barrier and the delivery device, and preferably also the liquid dispenser.

The active compound may comprise one or more active compounds, and may comprise a mixture of active compounds.

The active compounds may comprise one or more of NR, ascorbic acid (vitamin C) and/or peptides as examples only. The active compound(s) are beneficially water soluble in order that it is dissolved prior to application to the skin such that they may diffuse into the apertures and along the pathway(s) formed in the stratum corneum by the arrangement for providing a pathway into the biological barrier.

The substrate may carry a plurality of active compounds. The active compounds may be mixed, or alternatively be located in separate zones. The separate zones may be provided in pockets in the delivery device, for example between the first and second portions of the delivery device. Alternatively, or in addition, a plurality of active compound carrying substrates may be provided in the kit carrying different active compounds.

The substrate is preferably packaged in a sealed packaging which has the beneficial properties of being moisture resistant packaging. This is preferably in addition to the sealed housing. For some active compounds, for example Nicotinamide Riboside (NR), it is essential that the NR remains dry until shortly before application to the skin as if left for some hours in an environment with water (either in liquid or vapour form) then the NR will disassociate to form nicotinamide and ribose. This is particularly detrimental to the intended application of this active component as nicotinamide acts as an inhibitor for the sirtuin repair enzymes which is the opposite of the purpose of application of NR.

The apparatus for providing a pathway into the biological barrier is beneficially arranged to damage or ablate the outermost layer of the biological barrier. The outermost layer beneficially comprises the stratum corneum. The apparatus for providing the pathway into the biological barrier and the delivery device are preferably physically separate from each other. They can therefore be applied in sequence. This also allows the apparatus for providing the pathway into the biological barrier to be re-used.

The apparatus for providing a pathway into the biological barrier may comprise a device for administering a plurality of holes into the biological barrier. The device may comprise a microneedle device having a plurality of microneedles extending from a microneedle carrying substrate. Preferably the microneedle device comprises a patch.

The microneedle carrying substrate is beneficially a flexible substrate having a first side and a second opposing side, each microneedle comprising a head and a projection for penetrating the biological barrier extending from the head, wherein the projection at least partially extends through the flexible substrate towards the first side. The microneedle device may comprise a pad, roller, stamp for example.

The microneedle carrying substrate is preferably a flexible substrate having a first side and a second opposing side, each microneedle comprising a head and a projection for penetrating the biological barrier extending from the head, wherein the projection at least partially extends through the flexible substrate towards the first side. At least two projections preferably extend from each head. The head may comprise an elongate arm spacing apart the first and second projections.

The microneedle patch may be deformable to conform to the geometry of a user's finger. Alternatively, the microneedle patch may be pre-formed to conform to the geometry of a finger. The microneedle patch may at least partially receive a finger.

The microneedles have a longitudinal length, and the maximum longitudinal length of each of the microneedles projecting from the microneedle carrying substrate is preferably less than 0.5 mm, even more preferably less than 0.4 mm, and even more preferably less than 0.3 mm. A particularly preferred maximum dimension is approximately 0.25 mm which provides pathways into the skin without pain or bleeding. The diameter of each of the microneedles is preferably less than 0.125 mm and beneficially in the range of 100 µm to 80 µm.

The kit preferably further comprises a cover for application to the application zone after application of the active compound to the application zone. The cover beneficially increases permeation of the active compound into the skin. The cover may further comprise an active compound, preferably different to the active compound carried by the substrate.

The arrangement for providing a pathway into the biological barrier may comprise a chemical peel. This has the effect of reducing the barrier function of the stratum corneum to improve transfer of the active compound into the skin. A chemical peel may be provided in addition to a microneedle device.

Also according to the present invention there is a delivery device for delivering an active compound to a biological barrier arranged to carry an active compound in dried form.

The delivery device preferably comprises a material liquid absorbent material. The delivery device is preferably liquid permeable.

The delivery device preferably comprises a structure having a plurality of interstices therein for receipt of the dry active compound.

The delivery device may be termed a substrate for carrying the active compound.

The delivery device may comprise a first portion and a second portion and wherein the active compound is provided between the first and second portions. The first and second portions may be stacked. The first and second portions preferably define at least one pocket therebetween for receipt of the active compound. The first and second portions may be adhered at a peripheral edge. At least one of the first and second portions preferably comprises a foam material.

The substrate is preferably arranged to be drawn over a biological barrier. Therefore it is beneficial that the substrate is of a suitable size and configuration to be drawn over the skin of a subject. Alternatively the substrate may be held against the skin of a subject.

The active compound preferably comprises a precursor to nicotinamide adenine dinucleotide (NAD+). The active compound may comprise nicotinamide and/or a derivative of nicotinamide. The active compound may comprises one or more of nicotinamide riboside (NR) and nicotinamide mononucleotide (NMN).

The delivery device may comprise a patch. The patch may comprise an adhesive for adhering to a biological barrier. A portion of the patch may comprise an adhesive, such as a peripheral edge portion. This enables a peripheral edge portion to be held against a subject whilst the active compound is retained by another portion of the patch. An adhesive may for example comprise a hydrogel.

Also according to the present invention there is a method of delivering an active compound into a biological barrier comprising:
  forming a pathway into the biological barrier in an application zone;
  dissolving an active compound provided in dried form;
  applying the dissolved active compound to the application zone.

The method beneficially comprises a cosmetic method for improving the appearance of the skin.

The biological barrier preferably comprises skin. The method preferably comprises forming a plurality of pathways into the biological barrier, preferably stratum corneum of the skin.

The step of forming a plurality of pathways into the biological barrier comprises applying an arrangement for providing a pathway into the biological barrier to the application zone. The device preferably comprises a microneedle device having a plurality of microneedles extending from a microneedle carrying substrate, such that the plurality of microneedles project into the biological barrier in the application zone.

Other suitable arrangements for providing a pathway into a biological barrier are described above with respect to the kit and include for example a chemical peel. Other suitable techniques may comprise radio frequency ablation or microdermabrasion.

The active compound is preferably carried by the delivery device, which may be termed a substrate. The active compound is preferably dissolved while the active compound is on the delivery device, meaning dissolved active compound is applied to the skin by virtue of the delivery device and further handling is not required. Application of a liquid to the active compound beneficially dissolves the active compound into the liquid. The liquid having the dissolved active compound therein is beneficially carried by the delivery device.

The delivery device is beneficially suitable for being grasped by a user and presented to a user's skin, and preferably drawn over, held on or dabbed onto a user's skin.

A liquid dispenser is preferably provided for dispensing a liquid to the active compound carried by the first substrate. The step of applying liquid to the active compound beneficially causes the active compound to become dissolved in the liquid. Some active compounds may not dissolve in the liquid, but may alternatively become hydrated and/or activated by the liquid.

Application of the dissolved and/or hydrated active compound to the skin is preferably performed by wiping the delivery device over the application zone.

The method may further comprise the step of applying a cover to the application zone after application of the active compound.

The active compound is preferably delivered through the stratum corneum.

Active compound preferably refers to one or more active compounds.

BRIEF DESCRIPTION OF THE DRAWINGS

Aspects of the present invention will now be described by way of illustration only with reference to the accompanying Figures in which.

DETAILED DESCRIPTION OF THE PREFERRED EMBODIMENT

Figure 1:
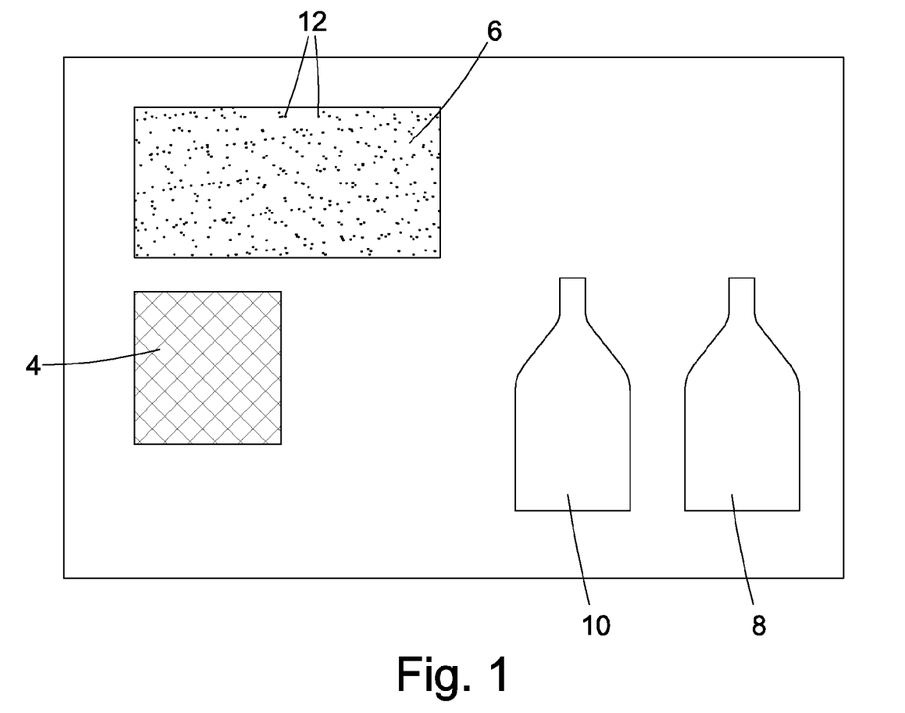
FIG. 1 is a schematic plan view of a kit according to an illustrative embodiment.

Referring to FIG. 1 there is a schematic representation of a kit according to an illustrative embodiment of the present invention. The kit comprises a housing 2 for housing the constituent components of the kit, where the constituents comprise an arrangement for providing a pathway into a biological barrier. Such an apparatus may take different forms such as a chemical peel, microdermabrasion element or device for administering holes into the skin. A chemical peel agent may comprise an acid and comprise one or more of lactic acid, glycolic acid, trichloroacetic acid and salicylic acid.

A device for administering holes into skin may take a variety of forms such as a roller, stamp, pad or patch having projections extending therefrom. An illustrative embodiment has been described whereby the device comprises a microneedle patch 4, described in more detail with respect to FIG. 3. The kit further comprises a delivery device, represented as a substrate 6 carrying one or more active compounds, a liquid dispenser 8 for dispensing hydrating fluid to the substrate 6 and a cleaning arrangement 10 for cleaning the device, preferably microneedle patch 4 after and/or prior to use.

In one embodiment the device for administering a plurality of holes into the skin may comprise a laser device. Such laser devices may be used in both professionally in salons or for home use. Another device may emit radio frequency to produce holes in the skin.

In the illustrative embodiment the delivery device 6 in the form of a substrate is arranged to carry a dry active compound 12. The active compound may be adhered to or otherwise held by the substrate. For example, the substrate 6 may comprise a fibrous or foam structure having interstices in which the dry active compound 12 is received. Alternatively or in addition, the active compound 12 may be dried from solution and effectively adhere to the second substrate. In an alternative form, the active compound 12 may be formed in a layer dispersed across a surface of the substrate 6. The substrate is beneficially of a material capable of absorbing liquid such that when liquid is applied it is capable of carrying liquid which in turn absorbs active compound carried by the second substrate for application to the skin. Such absorbent materials may comprise for example sponges, foams, woven materials or papers. The absorbent material may comprise an adhesive for temporary adhesion to the skin. This improves penetration of the active compound into the skin.

The delivery device 6 may take a variety of forms. The role of the delivery device is to deliver the active compound to the biological barrier. The delivery device 6 may comprise a patch, pad or may alternatively comprise a grip portion free of active compound and a head portion carrying the active compound, where the head portion may be subsequently brought into contact with liquid to enable dissolving and/or hydration of the active compound 12.

Other arrangements for carrying active compound in dried form may be provided where the active compound is dissolved prior to application to the application zone via a delivery device. For example dry active compound may be provided in a first container, and a solvent for dissolving the dry active compound may be provided in a second container wherein the contents of the first and second containers are mixed prior to transfer onto a delivery device such as a patch.

The delivery device 6 may take the form of a container having an aperture for dispensing the solution of active compound directly to the application zone, or via an intermediate patch for more controlled delivery of the solution. Further embodiments may comprise a single container having multiple chambers having dry active compound and solvent therein, where mixing may be achieved by twisting, breaking, snapping or otherwise disturbing a seal between the two chambers. The delivery device may include a chamber for carrying the dry active compound.

Figure 2:
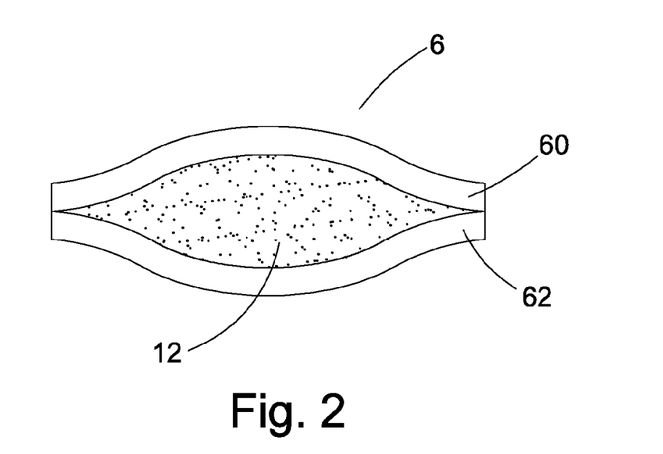
FIG. 2 is a schematic side view representation of a delivery device according to an illustrative embodiment of the present invention.

FIG. 2 is a schematic side representation of a delivery device 6 according to an illustrative embodiment. Presented is a first and second portion 60, 62 in the form of first and second sheets which are stacked to form a layered structure. The first and second portions 60,62 are adhered at a peripheral edge such that a pocket 64 is defined between the first and second portions 60, 62 in which the active compound 12 is received. The first and second portions 60, 62 are liquid permeable, meaning that upon application of a liquid the active compound is dissolved in the liquid and can be applied to the application zone of the user.

The active compound 12 may comprise a mixture of multiple different compounds. It is preferable that the active compound is a precursor to NAD+ and comprises nicotinamide or a nicotinamide derivative. A suitable example of one of the active compounds is Nicotinamide Riboside (NR). NAD+ is a molecule found in every cell in the body, being used to power metabolism, resist free radical and DNA damage and send signals within the cells. It enables the mitochondria to convert food consumed into energy required by the body to sustain all its functions. The active compound may comprise one or more of nicotinamide riboside (NR), nicotinamide mononucleotide (NMN), ascorbic acid (vitamin C), peptides, growth factors, anti-glycation actives, vitamins, sirtuin activating compounds such as resveratrol, polyphenols, and/or polyamines.

Healthy mitochondrial function is an important component of healthy human aging. As people age, levels of NAD+ declines substantially. This decline leaves people at greater risk for neuro and muscular degeneration, reduces cardiometabolic health and an individual's capacity for repair and resiliency. NAD+ is beneficial in increasing the amount of time people spend in good health, and NR and NMN in particular act to help the mitochondria within the cell to undergo cellular energy production.

Cellular energy not only fuels the most basic bodily functions, it also is necessary to defend against oxidative stress in the body, repair DNA damage, create the building blocks for DNA and RNA, and to activate 'longevity promoting' proteins called sirtuins. NR is an effective vitamin B3 at boosting NAD+ and activating sirtuins which act to improve mitochondrial activity to help prevent cellular damage due to free radicals. NR is capable of passing through cell walls where it then combines with phosphate and subsequently adenosine to form NAD+.

In an aqueous environment NR and NMN has been found to degrade within days, meaning that traditional forms of application to the skin through a cream show minimal effect. Thus in the present invention the active compound is provided in dried form on the substrate. The active compound 12 is hydrated preferably through application of liquid to the patch 6 from the liquid dispenser 8 to flow through pathways formed in the skin. This may be via the microneedles carried by the microneedle patch 4. The liquid may contain stable elements that help hydrate and/or improve the skin including hyaluronic acid, glycerol, some peptides, growth factors and/or vitamin A derivatives. The liquid may be a gel, lotion, emulsion or cream. Furthermore, the liquid may dependent upon desired effects could contain ingredients that temporarily alter the feeling or texture of the skin—for example by making it smoother or tighter (as the water or vehicle evaporates).

The cleaning arrangement 10 has been schematically represented as a fluid dispenser, where cleaning fluid is dispensed onto the microneedle patch. In addition, there may be provided wipes for wiping the cleaning fluid across the microneedle patch to ensure effective cleaning and/or drying. Alternatively however the cleaning arrangement may comprise wipes carrying cleaning material, or other suitable alternatives. The cleaning arrangement may also be integrated into a container for storing the microneedle patch 4.

The kit may further comprise a cover (not shown) for application to the application zone after application of the active compound to the application zone. The cover beneficially increases permeation of the active compound into the skin, by effectively sealing the active compound onto the skin such that permeation into the holes is achieved. The cover may be formed from a variety of materials, such as for example hydrogels. The cover may further comprise an active compound, preferably different to the active compound carried by the substrate. The substrate 6 or cover (not shown) may further comprise a neutralising agent for the any acid present from use of a chemical peel in providing the pathway into the biological barrier.

Figure 3A:
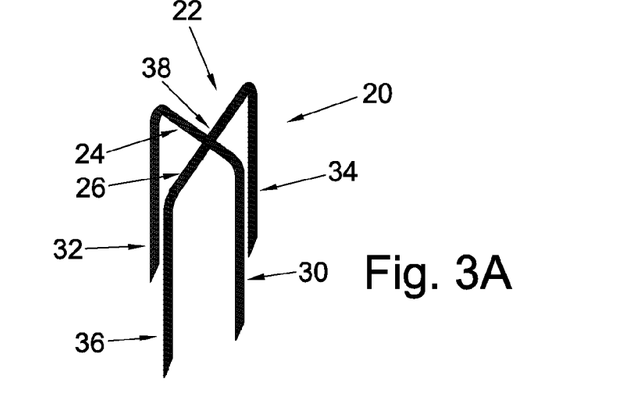
FIGS. 3a-c are schematic magnified representations of a partial microneedle patch for use with an illustrative embodiment of the present invention.
Figure 3B:
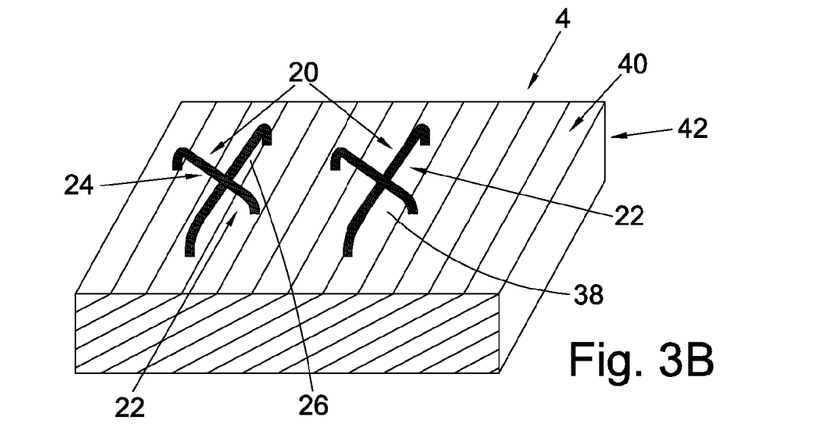

Referring to FIG. 3, an exemplary magnified microneedle arrangement 20 is presented in FIG. 2a and an exemplary partial microneedle patch 4 is presented in FIGS. 3b and c. The microneedle arrangement 20 comprises a head 22 in the form of a cross comprising a first arm 24 and second arm 26. First and second projections 30,32 extend from the distal ends of the first arm 24. From the distal ends of the second arm 26 third and fourth projections 34,36 extend. The benefit associated with additional projections extending from the head 22 is the further stability provided. It will be appreciated that a configuration of three or more projections provides improved stability. In the embodiment presented, the arms 24,26 overlap at an overlap zone 38 and are beneficially adhered at this point. First and second arms 24,26 are mutually perpendicular.

Figure 3C:
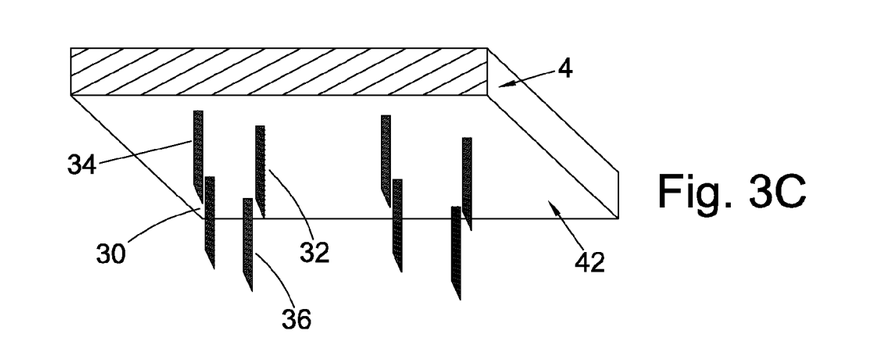

Referring to FIG. 3b, the head 22 can be seen abutting a second side 40 of a flexible substrate 42. In bottom perspective view as shown in FIG. 3c, the projections 30, 32, 34, 36 project through the flexible substrate 42 for penetration into the skin. It will be appreciated that the flexible substrate 42 may be made of a plurality of different flexible materials, for example silicone.

Figure 3D:
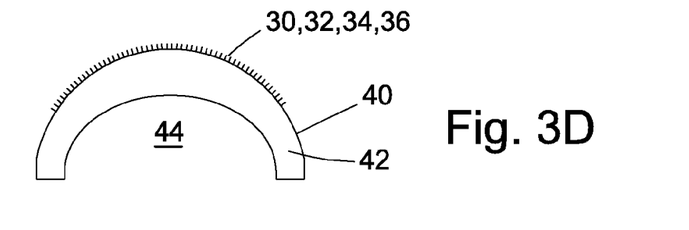
FIG. 3d is a schematic side view of a complete microneedle patch.

Referring to FIG. 3d, a microneedle patch 4 is schematically presented in side view and shows a receiving area 44 for receipt of a user's finger. The substrate 42 is flexible and adapts to the shape of a user's finger thereby optimising control of use.

Figure 4:
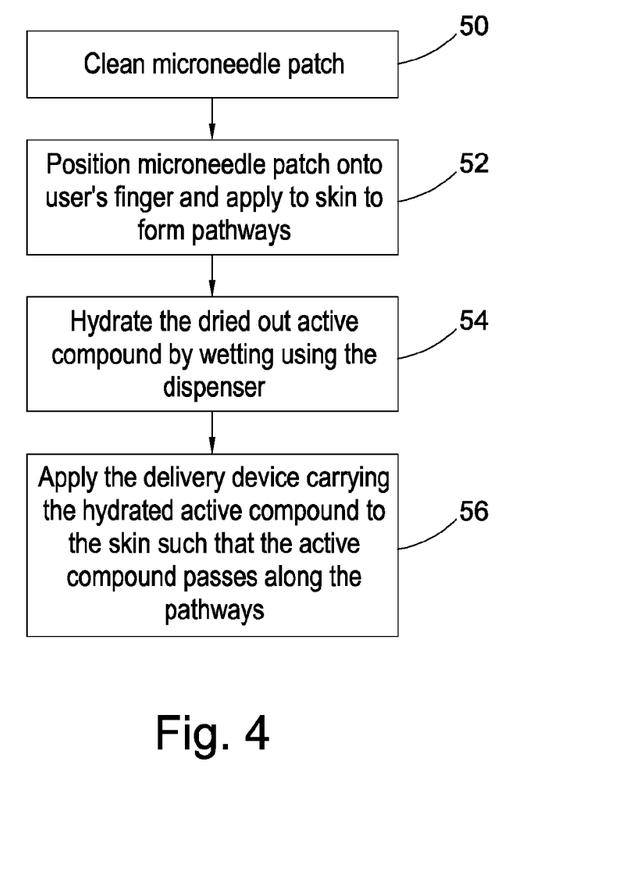
FIG. 4 is a schematic flow chart showing the operational steps for a method of delivering an active component to the skin.

Referring now to FIG. 4, a flowchart for a method of providing a cosmetic treatment to the skin is presented. If having already been previously used, the arrangement for providing a pathway into a biological barrier of a substrate in the exemplary form of a microneedle patch 4 is cleaned using the cleaning arrangement 10 as a first step 50. In step two 52 a user locates their finger into the receiving area 44 of the microneedle patch 4 and the microneedle patch 4 is applied to the desired areas of the skin, such as in the area beneath the eyes, by gently applying pressure, preferably in a rolling motion, to cause the projections 30, 32, 34, 36 to penetrate into the stratum corneum.

Having applied the microneedle patch to the desired areas of the skin the microneedle patch 4 is withdrawn and the delivery device 6 carrying the active compound 12 is hydrated using the fluid in the dispenser 8. It will be appreciated that with the relatively short time period between cleaning and/or application of the microneedle patch to the skin, hydrating the substrate carrying the active compound may be completed before, after or between the steps of cleaning and applying the microneedle patch 4 to the skin. The hydrated active compound then passes through the pathways formed in the skin by the microneedles. The delivery device 6 is then discarded. A cover may then be placed over the treated area and may carry further active compounds. The cover may comprise an adhesive for adhering the cover to the skin. The adhesive may be limited to a peripheral edge portion.

A set of instructions is beneficially provided in the kit. The instructions may define a treatment schedule. The kit may include multiple substrates carrying active compounds, whereby the strength or composition of the active compound differs. The instructions may define the treatment protocol including order of application and timings.

Aspects of the present invention have been described by way of example only and it will be appreciated to the skilled addressee that modifications and variations may be made without departing from the scope of protection afforded by the appended claims.

The invention claimed is:

1. An active compound delivery kit for enabling delivery of an active compound into the skin of a subject, the kit comprising:
   a microneedle device having a plurality of microneedles extending from a microneedle carrying substrate for providing a pathway in the form of a plurality of holes into skin of a subject in an application zone;
   an active compound provided in dry form; and
   a delivery device comprising a liquid absorbent carrier of the dry active compound, the delivery device for delivery of active compound in a dissolved form to the application zone;
   wherein the delivery device and the microneedle device are physically separate in the delivery kit and are applied in sequence; and
   wherein the active compound comprises one or more of nicotinamide riboside (NR) and nicotinamide mononucleotide (NMN).

2. The kit according to claim 1, wherein the active compound comprises one or more of: ascorbic acid (vitamin C), peptides, growth factors, anti-glycation actives, vitamins, retinoids, anti-oxidants, brightening agents, whitening agents, sirtuin activating compounds, polyphenols, and polyamines.

3. The kit according to claim 1, wherein the active compound is in powdered form.

4. The kit according to claim 1, wherein the delivery device comprises a patch.

5. The kit according to claim 1, wherein the delivery device comprises a structure having a plurality of interstices therein for receipt of the dry active compound.

6. The kit according to claim 1, wherein the delivery device comprises a first portion and a second portion and wherein the active compound is provided between the first and the second portion.

7. The kit according to claim 6, wherein the first and second portions are stacked.

8. The kit according to claim 1, further comprising a liquid dispensing arrangement for dispensing a liquid to the active compound in dry form for hydrating and/or dissolving the active compound to provide dissolved active compound.

9. The kit according to claim 1, further comprising:
- a cleaning arrangement for cleaning the arrangement for providing a pathway into the biological barrier; and/or
- a sealed housing for housing the arrangement for providing a pathway into the biological barrier and the delivery device.

10. The kit according to claim 1, wherein the active compound comprises one or more active compounds.

11. The kit according to claim 10, wherein the active compound comprises a plurality of active compound constituents, and each active compound constituent is located in a separate zone on the liquid absorbent carrier.

12. The kit according to claim 1, wherein:
- the microneedle device comprises a patch; and/or
- the microneedle carrying substrate is a flexible substrate having a first side and a second opposing side, each microneedle comprising a head and a projection for penetrating the biological barrier extending from the head, the projection at least partially extending through the flexible substrate towards the first side; and/or
- a maximum longitudinal length of each of the microneedles projecting from the microneedle carrying substrate is less than 2 mm, or than 0.5 mm, or less than 0.3 mm.

13. The kit according to claim 1, wherein the kit comprises a plurality of delivery devices comprising a second delivery device, wherein each subset carries a different active compound.

* * * * *